United States Patent [19]

Undheim et al.

[11] Patent Number: 5,629,293
[45] Date of Patent: May 13, 1997

[54] SINGLE CHAIN PEPTIDE COMPOUNDS HAVING HEMOREGULATORY ACTIVITY

[75] Inventors: Kjell Undheim, Sandvika, Norway; Peter Kremminger, Liuz; Michael Hartmann, Pettenbach, both of Austria

[73] Assignee: Nycomed Imaging AS, Oslo, Norway

[21] Appl. No.: 343,602

[22] PCT Filed: Jun. 2, 1993

[86] PCT No.: PCT/GB93/01172

§ 371 Date: Nov. 30, 1994

§ 102(e) Date: Nov. 30, 1994

[87] PCT Pub. No.: WO93/24524

PCT Pub. Date: Dec. 9, 1993

[30] Foreign Application Priority Data

Jun. 2, 1992 [GB] United Kingdom ............... 9211668

[51] Int. Cl.$^6$ ............... A61K 38/08; C07D 241/08; C07K 1/02; C07K 7/06
[52] U.S. Cl. ............... 514/17; 530/329; 530/330; 530/338; 544/408
[58] Field of Search ............... 544/408; 530/338, 530/343, 329, 330; 514/17

[56] References Cited

U.S. PATENT DOCUMENTS

| | | | |
|---|---|---|---|
| 3,778,426 | 12/1973 | Najjar | 530/330 |
| 4,171,299 | 10/1979 | Hamburger | 530/331 |
| 4,579,840 | 4/1986 | Hahn | 530/329 |
| 4,628,045 | 12/1986 | Hahn | 514/17 |
| 4,797,469 | 1/1989 | Diaz et al. | 530/329 |
| 4,816,449 | 3/1989 | Hahn | 514/17 |
| 5,015,470 | 5/1991 | Gibson | 514/17 |
| 5,112,811 | 5/1992 | Lenfant et al. | 530/330 |
| 5,312,812 | 5/1994 | Balazs et al. | 530/330 |
| 5,484,770 | 1/1996 | Laerum | 514/17 |

FOREIGN PATENT DOCUMENTS

| | | |
|---|---|---|
| 0359338 | 3/1990 | European Pat. Off. . |
| 0474456 | 3/1992 | European Pat. Off. . |
| WO-A-9310807 | 6/1993 | WIPO . |

OTHER PUBLICATIONS

Roberts et al, Basic Principles of Organic Chemistry, 2nd ed., published 1977 by W. A. Benjamin, Inc. (Menlo Park), pp. 1208–1210.
Bull. Soc. Chim. France, Nos. 5–6, issued 1976, Sakarellos et al, "Synthese de Peptides Substrats . . . ", pp. 781–788.
Chem. Pharm. Bull., vol. 25, No. 8, issued 1977, Yajima et al, "Studies on Peptides, LXXI, Synthesis of the . . . ", pp. 2048–2054.
Angew Chem. Int. Ed. Engl., vol. 30, No. 12, issued 1991, Wild et al, "Enantioselective and Diastereoselective . . . ", pp. 1685–1687.
J. Chem. Soc., Chem. Commun., No. 5, issued 1992, Kotha et al, "A New Synthetic Approach to Unusually Electron Rich . . . ", pp. 404–406.
Int. J. Peptide Protein Res., vol. 36, issued 1990, Cushman et al, "Synthesis of [β–(4–pyridyl)–1–oxide] . . . ", pp. 538–543.
Stryer, Biochemistry, 1988, New York, 18–20.
Schollkopf et al., Synthesis, vol. 9, Sep., 1986, Stuttgart, Germany, 737–740.
Laerum et al., Experimental Hematology, vol. 16, No. 4, May 1988, 274–280.
Tetrahedron, vol. 39, No. 12, issued 1983, Schollkopf, "Enantioselective Synthesis of Non–Proteinogenic . . . ", pp. 2085–2091.

Primary Examiner—Jeffrey E. Russel
Attorney, Agent, or Firm—Bacon & Thomas

[57] ABSTRACT

There is disclosed single chain peptide compounds, substituted at a Cα-atom of a non-terminal amino acid by a group—A which is defined in claim 1. The native α-side chain of the Cα atom bonded group to group —A absent. The peptide derivatives according to the invention are useful for inhibiting cell proliferation, especially myelopoietic and bone marrow cells.

14 Claims, No Drawings

SINGLE CHAIN PEPTIDE COMPOUNDS HAVING HEMOREGULATORY ACTIVITY

The present invention relates to the use of peptides having an inhibitory effect on cell proliferation, and to novel peptides having specific and/or general cell inhibitory effects.

The mammalian body contains cells having enormously diverse structures and functions, and the mechanisms of differentiation and development have been the focus of much study. It is known that for systems of cells having a continuous turnover the mechanism commonly involves a reservoir of pluripotent stem cells which divide and constantly supply new cells to the system. While initially homogeneous the stem cells supplied from the "reservoir" soon become committed to one or other morphology and subsequently develop into the required functional cells.

Examples of such stem cell systems are the haemopoietic system in bone marrow and the epithelial and epidermal systems.

The manipulation or control of stem cell division is of great potential therapeutically and much research continues to be devoted to elucidating the mechanisms involved and the chemical messengers responsible. To date several biomolecules have been identified as possessing a role in cell production and differentiation either by the stimulation or inhibition of a step within the process. Myelopoiesis has been particularly well studied in this regard and molecules involved in its control include: colony-stimulating factors (CSF) such as granulocyte colony-stimulating factor (G-CSF), macrophage colony-stimulating factor (M-CSF), granulocyte-macrophage colony-stimulating factor (GM-CSF), multi-lineage colony-stimulating factor (multi-CSF; IL-3) [see Metcalf, Science 229: 16 (1985)], interleukin 11 (IL-11) [see Paul et al Proc Natl Acad Sci USA 87: 7521 (1990)], Lactoferrin [see Broxmeyer et al Blood Cells 11: 429 (1986)], prostoglandins [see Pelus et al J. Immunol 140: 479 (1988)], acidic (H-subunit) ferritin [see Broxmeyer et al Blood 68: 1257 (1986)], interferons ($\alpha$, $\beta$ and $\gamma$) [see Pelus et al supra. and Broxmeyer et al J. Immunol 131: 1300 (1983)], tumor necosis factors ($\alpha$ and $\beta$) [see Broxmeyer et al J Immunol 136: 4487 (1986)], transforming growth factor-$\beta$ [see Ottman et al J Immunol 140: 2661 (1988)], and activin and inhibin [see Broxmeyer et al Proc Natl Acad Sci USA 86: 779 (1989)].

It has also been found that the haemoregulatory pentapeptide (pGlu-Glu-Asp-Cys-Lys SEQ ID NO 1) inhibits the proliferation of myelopoietic cells selectively [see Paukovits et al Z. Naturforsch 37: 1297 (1982)] and other peptides corresponding to a narrow general formula were discovered to exert a similar inhibitory effect in hemopoiesis [see EP-A-112656 and WO90/02753]. Oxidation of the peptide monomers resulted in dimeric molecules linked by a cysteine bridge and these dimeric molecules were found to stimulate myelopoiesis [see Laerum et al. Exp. Hematol 16: 274 (1988)]. The (pGlu-Glu-Asp-Cys-Lys SEQ IS NO 1)$_2$ dimer and other similar compounds are disclosed in WO-A-88/03535. Further dimeric peptide compounds are disclosed in EP-A-408371 in which the disulphide bond has been replaced by a carbon or carbon/sulphur bridge linking the selected peptide chains. The bridge is thus relatively stable to hydrolysis but is itself inert and incapable of participating in receptor-dimer interactions.

While we do not wish to be bound by theoretical considerations, it is presently believed that such peptide compounds interact with stromal cells in vivo and that the stromal cells are responsible for stimulating or inhibiting cellular division via other soluble factors. The dimers are thus believed to induce or promote stromatic production of stimulatory cellular regulatory factor(s) whilst the monomeric peptides may either inhibit that process or cause the production of factors which prevent or hinder cell division. Thus, according to current thinking, the stromal cells may act to amplify the stimulatory or inhibitory effects of the dimeric and monomeric peptides respectively.

There is a continuing need for peptide compounds capable of inhibiting cell proliferation usefully in vivo. In this regard it should be noted that different degrees of inhibition may be more appropriate to certain clinical situations than to others and, in particular, selective inhibition of individual cell types is important.

The present invention provides a peptide derivative comprising a single-chain hemoregulatory, for example haemopoesis-inhibiting, peptide wherein a C$\alpha$ atom of a non-terminal amino acid thereof is substituted by a group —A, the native $\alpha$-side chain being absent from said C$\alpha$ atom, where A is —CR$^A$R$^A$—Z where each R$^A$ is independently a hydrogen atom or a group —R$^{A"}$, —OR$^{A"}$, —SR$^{A"}$, —NR$^{A"}$R$^{A"}$, CONR$^{A"}$R$^{A"}$ or —COOR$^{A"}$;

R$^{A'}$ is a hydrogen atom or a group R$^{A"}$;

R$^{A"}$ is an alkyl, cycloalkyl, alkanoyl, hydroxyalkyl, anidine group, or a carbocyclic or heterocyclic group;

Z is a group —OR$^B$, —NR$^C$R$^C$, —CR$^D$R$^E$R$^F$ or a substituted or unsubstituted, aromatic or non-aromatic, carbocyclic or heterocyclic ring other than unsubstituted phenyl;

wherein each R$^B$ is a straight chained or branched, saturated or unsaturated hydrocarbon group such as an alkyl, aralkyl or aryl group, optionally substituted by one or more R$^A$ groups, where R$^A$ is as defined above, and optionally interrupted by one or more —N—, —O— or —S— heteroatoms;

R$^C$ is a hydrogen atom or a group R$^B$;

R$^D$ is a hydrogen atom or a group R$^F$;

R$^E$ is a hydrogen atom or a group R$^F$, or together with group R$^D$ forms a >C=O group; and R$^F$ is a group —R$^B$, —OR$^B$, —NR$^C$R$^C$ or —SR$^B$, or a hydroxy, carboxy, aminocarbonyl or alkoxy group, or is a methylene group linked to the nitrogen atom attached to the C$\alpha$ atom, or together with R$^D$ forms an alkylidene group, or is a hydrogen atom where one of R$^A$, R$^{A'}$, R$^D$ and R$^E$ is other than hydrogen.

Where any group R$^A$ or R$^B$ is a C-attached organic group it preferably contains 1 to 10 carbon atoms, especially 1 to 6 carbon atoms. Alkyl groups may be straight chained or branched and may be substituted by aryl groups having 6–10 carbon atoms (ie. forming an aralkyl group), alkoxy, hydroxy, acyloxy, amino, azido, acylamino, aminocarbonyl or carboxy groups. Aryl groups include 5- or 6-membered heterocyclic aryl groups having one or more heteroatoms selected from O, N or S such as furyl, imidazolyl, pyrrolyl, pyridinyl and thienyl groups. Substituents which may be present on aryl groups include C$_{1-6}$ alkyl groups, hydroxy and carboxy groups. Examples include methyl, ethyl, propyl, t-butyl, pentyl, carboxyethyl and benzyl groups.

In one embodiment, Z represents a substituted or unsubstituted, aromatic or non-aromatic, carbocyclic or heterocyclic ring other than unsubstituted phenyl.

Particularly preferred groups for Z include benzyl, indolyl, hydroxyphenyl, imidazolyl, naphthyl, thienyl, pyridinyl, furanyl, isoxazolyl, 3,5-dimethylisoxazolyl or cyclohexyl groups.

In another embodiment Z represents a group —OR$^B$ (where R$^B$ is as defined above) or —CHR$^D$R$^F$ (where R$^D$ represents a hydrogen atom or a group —CH$_3$; R$^F$ represents an alkyl group optionally substituted by hydroxyl, amino or azide groups; or R$^D$ and R$^F$ together form an alkylidine group).

Preferably both R$^A$ and R$^{A'}$ represent hydrogen so that —A is a group —CH$_2$—Z.

Any single chain peptide which exhibits a hemoregulatory effect is suitable as the peptide which is substituted in accordance with the invention.

Alternatively expressed, the invention provides compounds according to the present invention in which the said hemoregulatory peptide chain include those of formula:

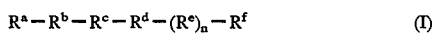

(I)

wherein R$^a$ represents

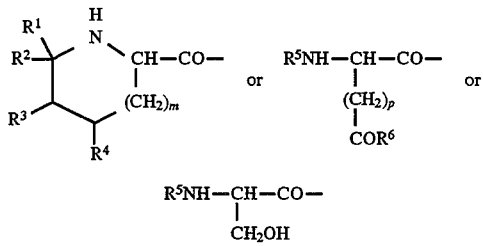

R$^b$ represents

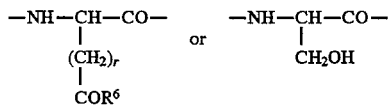

R$^c$ represents

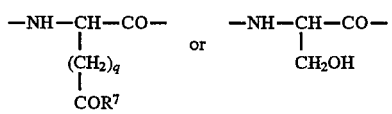

R$^d$ represents

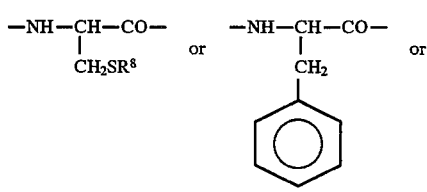

R$^e$ represents

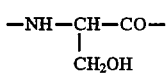

R$^f$ represents

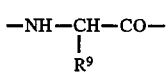

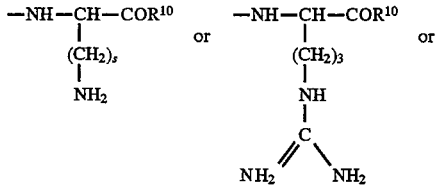

-continued

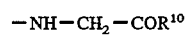

(wherein n and m independently represent 0 or 1;

p, q and r independently represent 1 or 2;

s represents 3 or 4;

R$^1$ and R$^2$ are both hydrogen atoms or together represent an oxo group;

R$^3$ and R$^4$ are both hydrogen atoms or together represent a carbon-carbon bond;

R$^5$ is hydrogen or an acyl group;

each R$^6$ and R$^7$ independently represent a hydroxy group or an amino group, but are preferably hydroxy groups, R$^8$ represents hydrogen; a C$_{2-6}$ alkyl group; a C$_{7-20}$ aralkyl group, which may carry one or more hydroxy, amino or methoxy substituents; or a metabolically labile S-protecting group;

R$^9$ represents hydrogen or a methyl group; and

R$^{10}$ represents a hydroxy or a substituted or unsubstituted amino group, the residue of the amino acid glutamine or a peptide having an N-terminal glutamine unit) and salts thereof.

All the said amino acid residues may be in either the D or the L form. The L-form of the amino acids is, however, preferred.

Where an N-terminal protecting group R$^5$ is present this may, as indicated above, be an acyl group having 1–20 carbon atoms, e.g. a lower alkanoyl group having 1–5 carbon atoms such as the acetyl group, or an aroyl or aralkanoyl group having 7 to 20 carbon atoms such as the benzoyl or phenylacetyl group.

R$^5$ may also be an acyl group derived from an amino acid or a peptide chain. In particular, R$^5$ may be an acyl group derived from serine or any of the peptides derived from the following amino acid sequence by removal of successive N-terminal amino acids: Lys-Ile-Ile-His-Glu-Asp-Gly-Tyr-Ser SEQ ID NO 2.

The terminal amino group of the overall peptide of formula (I) is preferably protected, e.g. by acylation with an alkanoyl, aralkanoyl or aroyl group.

Where R$^8$ is a C$_{2-6}$ alkyl group this may, for example, be an ethyl, butyl or hexyl group. When R$^8$ is an aralkyl group, this may conveniently be an arylmethyl group such as benzyl, diphenylmethyl or triphenylmethyl. Where R$^8$ is a metabolically labile group this may, for example, be an arylthio group having 5 to 10 carbon atoms, e.g. the pyridyl thio group, or an acyl group as defined above.

The compounds of the invention are preferably pentapeptides, that is n is preferably 0.

The cyclic groups in the R$^a$ residue are preferably five-membered, that is m is preferably 0.

Insofar as any of the peptides defined by formula I above are of low or negligible haemoregulatory activity, they may nevertheless be effective, in the peptide compound derivative according to the invention, in inhibiting cell proliferation.

In peptide compound derivatives formed from a peptide chain as described in formula I the substitution of the chain is desirably at R$^d$.

Particularly preferred peptide compound derivatives according to the present invention are those of formula II

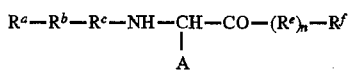

$$R^a\text{—}R^b\text{—}R^c\text{—}NH\text{—}\underset{\underset{A}{|}}{CH}\text{—}CO\text{—}(R^e)_n\text{—}R^f \qquad \text{II}$$

wherein $R^a$, $R^b$, $R^c$, $R^e$, $R^f$, A and n are all defined as above and the group —NH—CH—CO— is the derivatized form of $R^d$ which is attached to group —A in such a manner that it's native side chain is absent. The invention also includes compounds of formula II in which A together with the adjacent group —N—CH—CO— form a proline residue.

One especially preferred peptide compound of formula II is

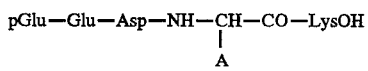

$$\text{pGlu—Glu—Asp—NH—}\underset{\underset{A}{|}}{CH}\text{—CO—LysOH}$$

where group —A is the group as discussed above.

The ability of the peptide derivatives of the invention to inhibit proliferation of a wide range of cells in addition to or even excluding the haemopoietic system is of value in medicine either where excessive cell proliferation requires treatment, as in psoriasis, or where cancer therapy would be likely to damage a particular cell population. Many cell types are particularly susceptible to the cytotoxic drugs or radiations used in anti-cancer therapy and one known technique is to use a drug to inhibit proliferation of cells such as those of the haemopoietic system during the anticancer therapy, followed by resumption of normal proliferation when the effect of the inhibitory drug has disappeared. The peptides of the present invention appear to have appropriately short biological half-lives for such therapy. Similarly, proliferation of selected populations of cells susceptible to cancer therapy may be inhibited together with the cancer cells themselves and the anti-cancer therapy is initiated only when the cancer cells have reached a susceptible phase of proliferation while the normal cells are in a less susceptible phase.

One type of cell proliferation occurs when cells such as bone marrow cells, phagocytes or granulocytes are stimulated by CSF drugs during therapy. Inhibition of cell growth can restore such cells to normal growth rates.

In many autoimmune diseases, the subject produces leucocytes active against their own tissues. By inhibiting leucocyte function, at least for a time, such autoimmune reactions may be correspondingly reduced.

Another clinical application will be in combination with the corresponding dimers or related myelopoiesis stimulators as disclosed in WO-A-88/03535 to induce alternating peaks of high and low activity in the bone marrow cells, thus augmenting the natural circadian rhythm of haemopoiesis. In this way, cytostatic therapy can be given at periods of low bone marrow activity, thus reducing the risk of bone marrow damage, while regeneration will be promoted by the succeeding peak of activity.

In general, in order to exert an inhibitory effect, the peptides of the invention may be administered to human patients orally or by injection in the dose range 0.001–100 mg, for example 1–5 mg, per 70 kg body weight per day. If administered intravenously or subcutaneously, the dose may be in the range 1–10 mg per 70 kg body weight per day, for example about 6 mg, for up to ten days. Nasal, topical (transdermal) or rectal administration is, of course, also feasible. In principle it is desirable to produce a concentration of the peptide of about $10^{-13}$M to $10^{-5}$M in the extracellular fluid of the patient.

According to a further feature of the present invention there are provided pharmaceutical compositions comprising as active ingredient one or more peptide compound derivatives as hereinbefore defined or physiologically compatible salts thereof, in association with a pharmaceutical carrier or excipient. The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1–10 mg, for example 1–5 mg of the peptide of formula (I) or salt thereof.

The present invention provides the peptide compounds and compositions described above for use in the inhibition of cell division, especially myelopoiesis and bone marrow regeneration. Use of the peptide compounds according to the invention in the manufacture of a medicament to inhibit cell division such as myelopoiesis and bone marrow regeneration also forms a further aspect of this invention.

According to a still further feature of the present invention there is provided a method of inhibition of cell division, especially myelopoiesis which comprises administering an effective amount of a compound or a pharmaceutical composition as hereinbefore defined to a subject.

A further major use of the new peptide compound derivatives, however, is in the production of material for immunological assay techniques. The peptide may then be covalently attached to a suitable high molecular carrier such as albumin, polylysine or polyproline in order to be injected into antibody-producing animals (e.g. rabbits, guinea pigs or goats). In vitro immunisation techniques may also be used. High specificity antisera are obtained by use of well known absorption techniques, using the high molecular carrier. By introducing radioactivity ($^3H$, $^{125}I$, $^{14}C$, $^{35}S$) into the peptide molecule, a radioimmuno assay can be designed and used for determining the peptide in the different biological fluids such as serum (plasma), urine and cerebrospinal fluid.

The peptides of the invention may be synthesised in any convenient way. Suitable methods for forming the amino acid units are described in, for example, "Synthesis of Optically Active α-Amino Acids" by Robert M. Williams (Pergamon Press, 1989). In general, the reactive side chain groups present (amino, thiol and/or carboxyl) will be protected during the coupling reactions of the overall synthesis but it is possible to leave some side chain groups unprotected (hydroxy groups, imidazole groups, primary amide groups, amide groups in cyclic amino acids like pyroGlu) during the entire synthetic procedure.

The final step will thus be the deprotection of a fully protected or a partly protected derivative of a peptide of the general formula I and such processes form a further aspect of the invention.

Schöllkopf et al have described the preparation of a variety of amino acids by the metallation and subsequent alkylation of bis-lactim ethers (see, for example, Tetrahedron 39: 2085 (1983) and Topics Curr Chem 109: 65 (1983)). An adaptation of this method has proved particularly useful for the preparation of the substituted amino acids which form the basis of the present invention. In particular, a bis-lactim ether derived from a valine-glycine dipeptide forms a useful starting compound for the substitution reaction which may be summarized as follows:

b) hydrolysing a bis-lactim dipeptide ether of step (a) to form an amino acid of formula $NH_2$—CH(A)—COOH wherein A is as defined above;

c) introducing the remaining amino acids in the peptide chain; and d) deprotecting any protected group.

The substituted bis-lactim dipeptide ethers and substituted α-amino acid produced by this technique form a further aspect of the present invention.

Additionally, the invention also covers amino-protected, hydroxyl protected, thiol protected and/or carboxyl protected peptide derivatives of the invention.

Once the substituted α-amino acid has been formed, then the remaining amino acids in the peptide chain can be introduced using conventional techniques.

In building up the peptide chains, one can in principle start either at the C-terminal or the N-terminal although only the C-terminal starting procedure is in common use.

Thus, one can start at the C-terminal by reaction of a suitably protected derivative of the first amino acid with a suitably protected derivative of the second amino acid. The first amino acid derivative will have a free α-amino group while the other reactant will have either a free or activated carboxyl group and a protected amino group. After coupling, the intermediate may be purified for example by chromatography, and then selectively N-deprotected to permit addition of a further N-protected and free or activated amino acid residue. This procedure is continued until the required amino acid sequence is completed.

Carboxylic acid activating substituents which may, for example, be employed include symmetrical or mixed anhydrides, or activated esters such as for example p-nitrophenyl ester, 2,4,5,trichlorophenylester, N-hydroxybenzotriazole ester (OBt), N-hydroxysuccinimidylester (OSu) or pentafluorophenylester (OPFP).

The coupling of free amino and carboxyl groups may, for example, be effected using dicyclohexylcarbodiimide

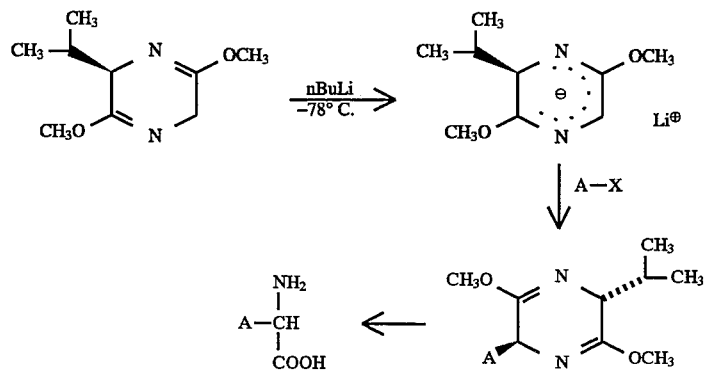

(wherein X is a leaving group, for example a bromine atom).

(S) α-amino acid derivatives can be prepared by this method if D-valine is initially used to form the bis-lactim ether. Equally, (R)-α-amino acid derivatives may be formed by the use of L-valine.

Thus, the present invention also provides a process for producing a peptide compound according to the invention comprising deprotecting a partially or fully protected derivative thereof.

The present invention further provides a process for producing a peptide compound according to the invention, comprising a) metallating and subsequently alkylating a bis-lactim ether to form a bis-lactim dipeptide ether;

(DCC). Another coupling agent which may, for example, be employed is N-ethoxycarbonyl-2-ethoxy-1,2-dihydroquinoline (EEDQ).

In general it is convenient to effect the coupling reactions at low temperatures, for example, −20° C. up to ambient temperature, conveniently in a suitable solvent system, for example, tetrahydrofuran, dioxan, dimethylformamide, methylene chloride or a mixture of these solvents.

It may be more convenient to carry out the synthesis on a solid phase resin support. Chloromethylated polystyrene (cross-linked with 1% divinyl benzene) is one useful type of support; in this case the synthesis will start the C-terminal, for example by coupling N-protected lysine to the support.

A number of suitable solid phase techniques are described by Eric Atherton, Christopher J. Logan, and Robert C. Sheppard, J. Chem. Soc. Perkin I, 538–46 (1981); James P. Tam, Foe S. Tjoeng, and R. B, Merrifield J. Am. Chem. Soc. 102, 6117–27 (1980); James P. Tam, Richard D. Dimarchi and R. B. Merrifield Int. J. Peptide Protein Res 16 412–25 (1980); Manfred Mutter and Dieter Bellof, Helvetica Chimica Acta 67 2009–16 (1984).

It is also possible for the coupling reactions to be performed in solution.

A wide choice of protecting groups for amino acids are known and are exemplified in Schröder, E., and Lübke, K., The Peptides, Vols. 1 and 2, Academic Press, New York and London, 1965 and 1966; Pettit, G. R., Synthetic Peptides, Vols. 1–4, Van Nostrand, Reinhold, New York 1970, 1971, 1975 and 1976; Houben-Weyl, Methoden der Organischen Chemie, Synthese von Peptiden, Band 15, Georg Thieme Verlag Stuttgart, NY, 1983; The Peptides, Analysis, synthesis, biology 1–7, Ed: Erhard Gross, Johannes Meienhofer, Academic Press, NY, San Fransisco, London; Solid phase peptide synthesis 2nd ed., John M. Stewart, Janis D. Young, Pierce Chemical Company.

Thus, for example amine protecting groups which may be employed include protecting groups such as carbobenzoxy (Z-), t-butoxycarbonyl (Boc-), 4-methoxy-2,3,6-trimethylbenzene sulphonyl (Mtr-), and 9-fluorenylmethoxycarbonyl (Fmoc-). It will be appreciated that when the peptide is built up from the C-terminal end, an amine protecting group will be present on the α-amino group of each new residue added and will need to be removed selectively prior to the next coupling step. For solid phase systems one particularly useful group for such temporary amine protection is the Fmoc group which can be removed selectively by treatment with piperidine in an organic solvent. For synthesis in solution, Boc- is a preferred protecting group, which can be introduced and removed in a conventional manner.

The amino acids or peptides often require to be silylated prior to protection eg. by addition of Fmoc in order to improve their solubility in organic solvents. Silylation and Fmoc protection reactions are summarized below:

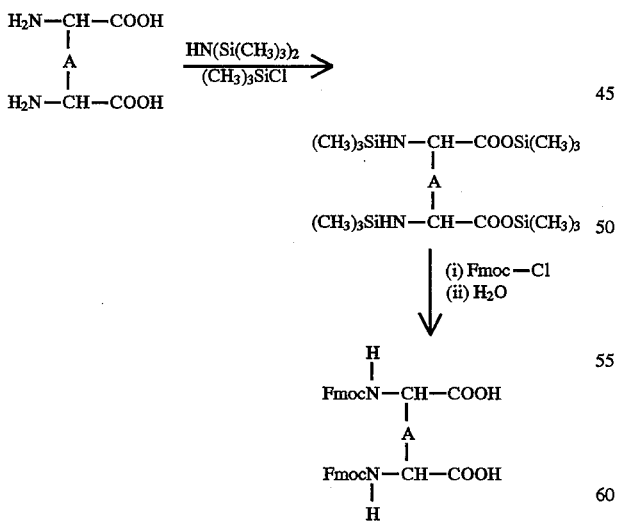

Carboxyl protecting groups which may, for example be employed include readily cleaved ester groups such as benzyl (—OBZl), p-nitrobenzyl (—ONB), or t-butyl (—tOBu) as well as the coupling on solid supports, for example methyl groups linked to polystyrene.

Thiol protecting groups include p-methoxybenzyl (Mob), trityl (Trt) and acetamidomethyl (Acm).

It will be appreciated that a wide range of other such groups exists as, for example, detailed in the above-mentioned literature references, and the use of all such groups in the hereinbefore described processes fall within the scope of the present invention.

A wide range of procedures exists for removing amine- and carboxyl-protecting groups. These must, however, be consistent with the synthetic strategy employed. The side chain protecting groups must be stable to the conditions used to remove the temporary α-amino protecting groups prior to the next coupling step.

Amine protecting groups such as Boc and carboxyl protecting groups such as tOBu may be removed simultaneously by acid treatment, for example with trifluoro acetic acid. Thiol protecting groups such as Trt may be removed selectively using an oxidation agent such as iodine.

The cysteine containing peptides may be synthesised by the methods described in the text with removal of all protecting groups including the thiol protecting groups as the last synthetic step.

The following Examples are given by way of illustration only.

EXAMPLE 1

(S)-2-(9-Fluorenylmethoxycarbonylamino)-5-phenyl-4-(E)-penten-1-oic-acid (S)-2-Amino-5-phenyl-4-(E)-penten-1-oic acid was prepared from (R)-(−)-2,5-dihydro-3,6-dimethoxy-2-isopropylpyrazine and cinnamyl bromide by analogy to the procedure described by U. Schollkopf, U. Groth and C. Deng in Angew. Chem. 93 (1981) 793. The amino acid (4.0 mmol) thus obtained, is added to a mixture of hexamethyl-disilazane (15 ml) and trimethylchlorosilane (2.0 ml), the mixture heated at 100° C. with stirring under $N_2$ overnight. Excess silylating reagent is then distilled off, the residue dissolved in $CH_2Cl_2$ (10 ml), a solution of 9-fluorenylmethoxycarbonyl chloride (4.1 mmol) in dry $CH_2Cl_2$ (5 ml) added, the mixture stirred at ambient temperature under $N_2$ for 3 hours, the $CH_2Cl_2$ evaporated, the residue dissolved in THF (9 ml) and water (1 ml), the solution stirred for 30 minutes, evaporated, the residue dissolved in EtOAc, dried ($MgSO_4$) and evaporated to yield the title compound for the subsequent peptide synthesis.

EXAMPLE 2

(2S,4R,5R)-N-9-Fluorenylmethyloxycarbonyl-N'-benzyloxycarbonyl-4,5-dihydroxy-4,5-O,O-isopropylidenelysine a) (2R,3R)-1-Bromo-4-[(2R,5S)-3,6-dimethoxy-2-isopropyl-2,5-dihydro-5-pyrazinyl]-2,3-dihydroxy-2,3-O,O-isopropylidene-butane (2R)-2,5-Dihydro-3,6-dimethoxy-2-isopropylpyrazine (3.24 g, 17.36 mmol) was dissolved in 60 ml anhydrous THF and the solution was cooled to −78° C. A solution of BuLi in hexane (10.85 ml, 17.36 mmol) was added and the solution was stirred for 30 minutes. After addition of 7.8 ml 1,3-dimethyl-2-imidazolidinone stirring was continued for an additional 15 minutes. A solution of (2R,3R)-1,4-dibromo-2,3-dihydroxy-2,3-O,O-isopropylidenebutane (5.0 g, 17.36 mmol) in 10 ml THF was added dropwise and the solution came to ambient temperature overnight. After hydrolysis with phosphate buffer (pH 7) the reaction mixture was extracted several times with diethyl ether, the organic solutions dried (MgSO$_4$), concentrated and the residue purified by flash chromatography (hexane/ethyl acetate 9/1).

Yield: 3.00 g (44.1%).

$^1$H NMR (CDCl$_3$) δ: 0.7(d,3H), 1.04 (d,3H), 1.40 (s,3H), 1.41 (s,3H), 1.95–2.30 (m,3H), 3.40–3.58 (m,2H), 3.68 (s,3H), 3.70 (s,3H), 3.97 (dd,1H), 4.03–4.20 (m,3H).

$^{13}$C NMR (CDCl$_3$) δ: 16.74, 19.03, 27.29, 27.46, 31.88, 32.66, 37.83, 52.40, 52.42, 52.55, 60.76, 79.80, 109.22, 163.21, 164.00 FAB-MS signal at m/z 391.2 (72), 141.1 (100).

b) (2R,3R)-1-Azido-4-[(2R,5S)-3,6-dimethoxy-2-isopropyl-2,5-dihydro-5-pyrazinyl]-2,3-dihydroxy-2,3-O,O-isopropylidene-butane (2R,3R)-1-Bromo-4-[(2R,5S)-3,6-dimethoxy-2-isopropyl-2,5-dihydro-5-pyrazinyl]-2,3-dihydroxy-2,3-isopropylidenebutane (5.51 g, 14.11 mmol) were dissolved in 50 ml DMF and 2.93 g NaN$_3$ (45 mmol) and 0.1 g NBu$_4$I were added. The solution was kept between 70° and 80° C. overnight and diluted with 50 ml water. After extraction with chloroform the organic layers were collected and dried (MgSO$_4$). The residue was purified by flash chromatography (hexane/ethyl acetate 7/3).

Yield: 4.06 g (81.5%).

$^1$H NMR (CDCl$_3$) δ: 0.68 (d,3H), 1.03 (d,3H), 1.40 (s,3H), 1.42 (s,3H), 1.95–2.30 (m,3H), 3.20–3.80 (m,2H), 3.65 (s,3H), 3.68 (s,3H), 3.95 (dd,1H), 4.00–4.15 (m,3H).

$^{13}$C NMR (CDCl$_3$) δ: 16.72, 19.02, 26.92, 27.27, 31.85, 37.52, 52.10, 52.36, 52.41, 52.47, 60.70, 75.09, 79.64, 109.13, 163.17, 164.00 FAB-MS signal at m/z 354.3 (100), 141.1 (75).

c) (2R,3R)-1-Benzyloxycarbonylamino-4-[(2R,5S)-3,6-dimethoxy-2-isopropyl-2,5-dihydro-5-pyrazinyl]-2,3-dihydroxy-2,3-O,O-isopropylidene-butane (2R,3R)-1-Azido-4-((2R,5S)-3,6-dimethoxy-2-isopropyl-2,5-dihydro-5-pyrazinyl)-2,3-dihydroxy-2,3-O,O-isopropylidenebutane (3.57 g, 10.12 mmol) was dissolved in 60 ml EtOH and 1.3 g Pd/C were added. The solution was purged with argon. Hydrogen was bubbled through the solution and it was kept under hydrogen overnight and filtered through celite. The residue was dried under vacuum and dissolved in 30 ml dioxane. 15 ml 1M NaHCO$_3$ solution (15 mmol) were added and 1.84 ml CbzCl (13 mmol) were added at 0° C. The solution was stirred at this temperature for 1 hour, diluted with water and extracted with chloroform. The residue was purified by flash chromatography (hexane/ethyl acetate 8/2).

Yield: 2.20 g (44.1%).

$^1$H NMR (CDCl$_3$) δ: 0.67 (d,3H), 1.03 (d,3H), 1.35 (s, 3H), 1.38 (s,3H), 1.90–2.05 (m,1H), 2.10–2.30 (m,2H), 3.30–3.55 (m,2H), 3.64 (s,3H), 3.68 (s,3H), 3.92–4.15 (m,4H), 5.09 (s,2H), 5.45 (m,1H), 7.26–7.38 (m,5H). $^{13}$C NMR (CDCl$_3$) δ: 16.70, 19.05, 27.17, 31.83, 37.69, 42.94, 52.26, 52.41, 52.52, 60.65, 66.72, 75.69, 79.41, 108.61, 128.02, 128.07, 128.47, 136.54, 156.40, 163.24, 164.11 FAB-MS signal at m/z 462.3 (56), 141.1 (47), 91.0 (100) C$_{24}$H$_{35}$N$_3$O$_6$ (461.6): Calc.: C, 62.45; H, 7.64; N, 9.10 Found: C, 62.99; H, 7.67; N, 8.77 d) (2S,4R,5R)-N'-Benzyloxycarbonyl-4,5-dihydroxy-4,5-O, O-isopropylidene-lysine methyl ester (2R,3R)-1-Benzyloxycarbonylamino-4-[(2R,5S)-3,6-dimethoxy-2-isopropyl-2,5-dihydro-5-pyrazinyl]-2,3-dihydroxy-2,3-O,O-isopropylidenebutane (0.5 g, 1.08 mmol) was dissolved in 5 ml dioxane and 4.20 ml 0.5M HCl (2.10 mmol) were added dropwise and stirred under argon at ambient temperature for 5 hours. Ammonia solution was added until pH 9 was reached, and the solution was extracted with chloroform, dried (MgSO$_4$), and the valine methyl ester was removed by bulb-to-bulb distillation (0.05 Torr, 25° C.). Yield: 0.40 g (100%).

$^1$H NMR (CDCl$_3$) δ: 1.35 (s,6H), 1.70–2.20 (m,4H), 3.20–3.60 (m,3H), 3.70 (s,3H), 3.73–3.90 (m,2H), 5.09 (s,2H), 5.32 (m, 1H), 7.26–7.40 (m, 5H). $^{13}$C NMR (CDCl$_3$) δ: 27.01, 27.05, 37.56, 42.11, 51.99, 52.38, 66.79, 75.79, 79.82, 108.99, 128.00, 128.44, 136.39, 156.46, 175.30

(2S,4R,5R)-N'-Benzyloxycarbonyl-4,5-dihydroxy-4,5-O,O-isopropylidene-lysine (2S,4R,5R)-N'-Benzyloxycarbonyl-4,5-dihydroxy-4,5-O, O-isopropylidenelysine methyl ester (0.40 g , 1.08 mmol) was dissolved in 3.5 ml water and 4 ml dioxane and cooled to 0° C. 0.54 ml 2N LiOH solution (1.08 mmol) were added, and the solution was stirred under argon overnight. TLC control showed quantitative formation of (2S,4R,5R)-N'-benzyloxycarbonyl-4,5-dihydroxy-4,5-isopropylidenelysine. This crude solution was directly used for the next step.

(2S,4R,5R)-N-9-Fluorenylmethyloxycarbonyl-N'-benzyloxycarbonyl-4,5-dihydroxy-4,5-O,O-isopropylidene-lysine 2.5 ml 1M NaOH solution (2.5 mmol) and a solution of 0.518 g 9-fluorenyloxycarbonylchloride (2.00 mmol) in 3 ml dioxane were added to a crude solution of (2S,4R,5R)-N'-benzyloxycarbonyl-4,5-dihydroxy-4,5-isopropylidenelysine and the mixture stirred overnight. The solution was acidified to pH 2 by addition of a KHSO$_4$-solution, extracted with ethyl acetate, dried (MgSO$_4$), and the residue was purified by flash chromatography (chloroform/MeOH 8/2).

Yield: 310 mg (50.0%).

$^1$H NMR (DMSO/D$_2$O) δ: 1.19 (s,3H), 1.22 (s,3H), 1.60–2.10 (m,2H), 2.90–3.30 (m,2H), 3.50–4.00 (m, 3H), 4.00–4.40 (m,3H), 4.95 (s,2H), 7.20–8.00 (m,13H). $^{13}$C NMR (DMSO/D$_2$O) δ: 27.59, 27.81, 37.14, 43.15, 53.94, 65.92, 66.01, 76.98, 80.16, 108.40, 120.61, 125.67, 125.79, 127.66, 128.16, 128.22, 128.32, 128.89, 137.55, 141.18, 144.36, 156.14, 156.87, 176.09 FAB-MS signal at m/z 497.1 (3), 429.1 (4), 179.1 (31), 91.0 (64) C$_{32}$H$_{34}$N$_2$O$_8$ (574.6): Calc.: C, 66.89; H, 5.96; N, 4.88 Found: C, 62.53; H, 5.60; N, 5.03

EXAMPLE 3

(S)-2-(9-Fluorenylmethyloxycarbonylamino)-6-azidohexanoic acid a) 1-Bromo-4-[(2R,5)-3,6-dimethoxy-2-isopropyl-2,5-dihydro-5-pyrazinyl]-butane (2R)-2,5-Dihydro-3,6-dimethoxy-2-isopropylpyrazine (3.76 g, 20.43 mmol) was dissolved in 60 ml anhydrous THF and the solution was cooled to −78° C. A solution of nBuLi in hexane (20.43 mmol, 12.77 ml) was added and the solution was stirred for 30 minutes. A solution of 1,4-dibromobutane (4.41 g, 20.43 mmol) in 10 ml THF was added dropwise and the solution came to ambient temperature overnight. After hydrolysis with phosphate buffer (pH 7) the reaction mixture was extracted several times with diethyl ether, the organic solution dried (MgSO$_4$) and the residue was purified by flash chromatography (hexane/ethyl acetate 9/1).

Yield: 3.88 g (59.6%).

$^1$H NMR (CDCl$_3$) δ: 0.68 d,3H),1.04 (d,3H), 1.23–1.47 (m,2H), 1.63—1.9. (m,4H), 2.25 (m,1H), 3.38 (t,2H), 3.67 (s,3H), 3.68 (s,3H), 3.90–4.05 (m,2H); $^{13}$C NMR (CDCl$_3$) δ: 16.58, 19.03, 23.29, 31.75, 32.63, 33.13, 33.58, 52.33, 55.13, 60.78, 163.60.

b) 1-Azido-4-[(2R,5S)-3,6-dimethoxy-2-isopropyl-2,5-dihydro-5-pyrazinyl]-butane

1-Bromo-4-[(2R,5S)-3,6-dimethoxy-2-isopropyl-2,5-dihydro-5-pyrazinyl]-butane (3.81 g, 11.95 mmol) were dissolved in 40 ml DMF and 3.25 g NaN$_3$ (50 mmol) and 0.1 g NBu$_4$I were added. The solution was kept between 70° and 80° C. overnight and diluted with 50 ml water. After extraction with chloroform the organic layers were collected and dried (MgSO$_4$). The residue was purified by flash chromatography (hexane/ethyl acetate 9/1).

Yield: 2.17 g (64.6%).

$^1$H NMR (CDCl$_3$) δ: 0.68 (d,3H), 1.04 (d,3H), 1.20–1.50 (m,2H), 1.53–1.91 (m,4H), 2.26 (m,1H), 3.25 (t,2H), 3.68 (s,3H), 3.69 (s,3H), 3.90–4.07 (m,2H). $^{13}$C NMR (CDCl$_3$) δ: 16.58, 19.05, 21.83, 28.72, 31.76, 33.56, 51.32, 52.35, 55.16, 60.79, 163.63.

c) Methyl(S)-2-amino-6-azidohexanoate

1-Azido-4-[(2R,5S)-3,6-dimethoxy-2-isopropyl-2,5-dihydro-5-pyrazinyl]butane (2.17 g, 7.72 mmol) was dissolved in 30 ml dioxane and a solution of 1.28 ml conc. HCl in 30 ml water (15.45 mmol) was added dropwise, the mixture stirred under argon at ambient temperature overnight. Ammonia solution was added until pH 9 was reached, the solution extracted with chloroform, dried (MgSO$_4$), and the valine methyl ester was removed by bulb-to-bulb distillation (0.05 torr, 25° C.).

Yield: 1.44 g (100%)

$^1$H NMR (CDCl$_3$) δ: 1.40–1.87 (m,8H), 3.28 (t,2H), 3.43 (dd,1H), 3.73 (s,3H). $^{13}$C NMR (CDCl$_3$) δ: 22.93, 28.63, 34.36, 51.22, 51.98, 54.26, 176.37.

d) (S)-2-Amino-6-azidohexanoic acid

Methyl-(S)-2-amino-6-azidohexanoate (1.44 g, 7.73 mmol) was dissolved in 4 ml dioxane and cooled to 0° C. 3.87 ml 2N LiOH solution (7.74 mmol) was added, and the solution was stirred under argon overnight. TLC control showed quantitative formation of (S)-2-amino-6-azidohexanoic acid. This crude solution was used in the next step.

e) (S)-2-(9-Fluorenylmethyloxycarbonylamino)-6-azidohexanoic acid 11.6 ml 1N NaHCO$_3$ solution (11.6 mmol) and a solution of 3.00 g 9-fluorenyloxycarbonylchloride (11.6 mmol) in 12 ml dioxane were added to the crude solution of (S)-2-amino-6-azidohexanoic acid (7.73 mmol) and stirring under argon was continued overnight. The solution was acidified to pH 2 by addition of a KHSO$_4$-solution, extracted with ethyl acetate, dried (MgSO$_4$), and the residue was purified by flash chromatography (hexane/ethyl acetate/acetic acid 7/3/0.5).

Yield: 2.00 g=65.6%

$^1$H NMR (DMSO) δ: 1.20–1.80 (m,2H), 3.31 (t,2H), 3.94 (m,1H), 4.27 (m,3H), 7.20–8.00 (m,8H). $^{13}$C NMR (DMSO) δ: 23.32, 28.26, 30.73, 47.10, 50.94, 54.09, 66.01, 120.48, 125.65, 127.44, 128.02, 141.11, 144.19, 144.25, 156.54, 174.22.

EXAMPLE 4

(S)-N-(9-Fluorenylmethyloxycarbonyl)-O-methyl-serine a) (2R,5S)-3,6-Dimethoxy-5-(methoxymethyl)-2-isopropyl-2,5-dihydropyrazine To a solution of (R)-2,5-dihydro-3,6-dimethoxy-2-isopropyl-pyrazine (5.53 g, 30 mmol) in anhydrous THF (80 ml) a 1.6M solution of n-BuLi in hexane (10.85 ml, 17.36 mmol) was added at −78° C. After 30 minutes a solution of bromomethyl methyl ether (4.5 g, 36 mmol) in THF (20 ml) was added dropwise. The reaction mixture was allowed to come to 20° C. overnight and was quenched by addition of 1M phosphate buffer (pH 7, 80 ml). The turbid mixture was stirred for 10 minutes, diluted with water (250 ml) and diethyl ether (180 ml). The layers were separated and the aqueous phase extracted with diethyl ether (2×150 ml). The combined organic layer was dried (Na$_2$SO$_4$), concentrated and purified by flash chromatography (silica gel; hexane:diethyl ether 5:1) to yield 5.61 g. To remove final impurities of the other diastereomer the material was crystallized from acetonitrile at −30° C. and the cold precipitate redissolved in CH$_2$Cl$_2$, dried (Na$_2$SO$_4$) and concentrated.

Yield 4.24 g (18.6 mmol, 62%).

$^1$H NMR (CDCl$_3$) δ: 4.05 (q, 1H, J 3.5 Hz), 3.99 (t, 1H, J 3.5 Hz), 3.80–3.64 (m, 8H), 3.34 (s, 3H), 2.29 (dsept, 1H, J 3.5, 7.0 Hz), 1.05 (d, 3H), 0.68 (d, 3H). $^{13}$C NMR (CDCl$_3$) δ164.79, 161.58, 74.13, 60.76, 59.51, 56.82, 52.42. FAB-MS signal at m/z 229 [M$^+$+1]. C$_{11}$H$_{20}$N$_2$O$_3$ (228.29).

b) Methyl(S)-2-(9-fluorenylmethyloxycarbonylamino)-3-methoxypropionate

To a solution of (2R,5S)-3,6-dimethoxy-5-(methoxymethyl)-2-isopropyl-2,5-dihydropyrazine (2.1 g, 9.2 mmol) in dioxane (18 ml) 1M HCl (18.4 ml), 18.4 mmol) was added and the mixture stirred at ambient temperature overnight. The volatile components were evaporated, the residue redissolved in dioxane and again evaporated. The crude residue was dissolved dioxane and FmocCl (5.71 g, 2.21 mmol) was added. After 2 minutes 1M NaHCO$_3$ (44.2 ml, 44.2 mmol) was added. After 15 minutes the mixture was diluted with water (50 ml) and CHCl$_3$ (100 ml). The layers were separated and the aqueous phase extracted with CHCl$_3$ (2×75 ml). The combined organic layer was dried (Na$_2$SO$_4$), concentrated and purified by flash chromatography (silica gel; hexane: ethyl acetate 2:1).

Yield 2.68 g (7.54 mmol, 82%).

$^1$H NMR (300 MHz, CDCl$_3$) δ7.78 (d,2H, J 7 Hz), 7.63 (t, 2H, J 7 Hz), 7.41 (t, 2H, 7 Hz), 4.56–4.35 (m, 3H), 4.25 (t, 1H, J 3.0, 9.3 Hz), 3.84 (dd, 1H, J 3.0, 9.3 Hz), 3.70 (s, 3H), 3.65 (dd, 1H, J 3.6, 9.3 Hz), 3.36 (s, 3H). $^{13}$C NMR (75 MHz, CDCl$_3$) δ170.77, 156.01, 143.88, 143.75, 141.25, 127.66, 127.02, 125.12, 125.07, 119.92, 72.27, 67.11, 59.23, 54.37, 53.44, 52.54, 47.12.

c) (S)-(9-Fluorenylmethyloxycarbonylamino)-3-methoxypropionic acid

To a solution of methyl (S)-(9-fluorenylmethyloxycarbonylamino)-3-methoxypropionate (2.18 g, 6.13 mmol) in dioxane (31 ml) 6M HCl (31 ml, 184 mmol) was added. This mixture was allowed to cool down and concentrated. The residue was purified by flash chromatography (silica gel; hexane: ethyl acetate: acetic acid (10:10:1).

Yield: 1.91 g (5.60 mol, 91%) after lyophilization.

$^1$H NMR (DMSO-d$_6$) δ7.87 (d, 2H, J 7.5 Hz), 7.74 (d, 2H, J 7.5 Hz), 7.41 (dt, 2H, J 0.6 Hz, 7.5 Hz), 7.31 (dt, 2H, J 0.6 Hz, 7.5 Hz), 4.29–4.19 (m, 4H), 3.65–3.54 (m, 2H), 3.24 (s, 3H). $^{13}$C NMR (DMSO-d$_6$): δ172.07, 156.46, 144.23, 144.21, 141.11, 128.03, 127.46, 125.73, 120.48, 71.80, 66.19, 58.60, 54.47, 47.05.

EXAMPLE 5

(S)-6-(Benzyloxycarbonylamino)-2,(9-fluorenylmethyloxy-carbonylamino)-hex-4-ynoic acid a) 1-Chloro-4-[(2R,5S)-3,6-diethoxy-2-isopropyl-2,5-dihydro-5-pyrazinyl]but-2-yne:

To a solution of (R)-2,5-dihydro-3,6-diethoxy-2-isopropylpyrazine (21.23 g, 100 mmol) in THF (200 ml) 1.6M n-BuLi (62.5 ml, 100 mmol) was added dropwise at −78°C. After 30 minutes this solution was transferred to a solution of 1,4-dichlorobut-2-yne (49.2 g, 400 mmol) in THF (400 ml) at −78° C. The mixture was allowed to come to 20° C. overnight. The reaction was quenched by addition of 1M phosphate buffer solution (250 ml). The mixture was diluted with diethyl ether (300 ml) and water (300 ml). The aqueous layer was separated and extracted with diethyl ether (2×300 ml). The combined organic layer was dried ($Na_2SO_4$), filtered, concentrated and purified by flash chromatography (silica gel; hexane:diethyl ether 10:1).

Yield: 24.8 g (83 mmol, 83%).

$^1$H NMR ($CDCl_3$): δ4.39–4.00 (m, 8H), 2.78 (m, AA'X, 2H), 2.30 (dsept, 1H, J 3.5, 9.5 Hz), 1.38–1.20 (m, 6H), 1.05 (d, 3H, 7 Hz), 0.70 (d, 3H, 7 Hz). $^{13}$C NMR ($CDCl_3$): δ161.03, 159.25, 83.76, 60.90, 54.21, 31.68, 30.95, 25.48, 20.62, 19.03, 15.85, 14.21.

b) 1-Azido-4-[(2R,5S)-3,6-diethoxy-2-isopropyl-2,5-dihydro-5-pyrazinyl]but-2-yne A solution of 1-chloro-4-[(2R,5S)-3,6-diethoxy-2-isopropyl-2,5-dihydro-5-pyrazinyl]but-2-yne (19.4 g, 65 mmol) and tetrabutylammonium iodide (2 g) in anhydrous DMF (200 ml) was stirred overnight at 20° C. Most of the DMF was removed at reduced pressure (0.01 torr). The residue was partitioned between diethyl ether (250 ml) and water (250 ml). The aqueous layer extracted with ether (2×250 ml). The combined organic layer was dried ($Na_2SO_4$), concentrated and the residue purified by flash chromatography (silica gel; hexane:diethyl ether 8:1).

Yield: 18.06 g (59 mmol, 91%).

$^1$H NMR ($CDCl_3$) δ4.25–3.99 (m, 4H), 3.84 (m, 6H), 3.84 (m, 2H), 2.83–2.77 (m, AA'X, 2H), 2.33–2.26 (m, 1H), 1.35–1.27 (m, 6H), 1.05 (d, 3H, J 7.2 Hz), 0.71 (d, 3H, J 7.2 Hz). $^{13}$C NMR ($CDCl_3$) δ164.24, 161.16, 84.54, 73.50, 61.00, 60.74, 54.31, 40.20, 31.84, 25.31, 19.03, 16.62, 14.27, 14.21.

c) 1-Benzyloxycarbonylamino-4-[(2R,5S)-3,6-diethoxy-2,5-dihydro-2-isopropyl-5-pyrazinyl]but-2-yne To a solution of 1-azido-4-[(2R,5S)-3,6-diethoxy-2-isopropyl-2,5-dihydro-5-pyrazinyl]but-2-yne (3.6 g, 11.8 mmol) in THF (236 ml) triphenylphosphine (3.7 g, 14.16 mmol) and $H_2O$ (680 ml, 37.8 mmol) were added at 20° C. Immediate $N_2$-evolution was observed. The reaction mixture was stirred for 2 hours and then concentrated. To a solution of the residue in dioxane (29 ml) 1M $NaHCO_3$ (14.2 ml, 14.2 mmol) and Cbz-chloride (2.42 g, 14.2 mmol) were added at 0° C. The mixture was kept at this temperature for 1 hour, then extracted with diethyl ether (3×50 ml). The combined organic layer was dried ($Na_2SO_4$), filtered, concentrated and purified by flash chromatography (silica gel; hexane:ethyl acetate 4:1).

Yield: 4.1 g (9.92 mmol, 84%).

$^1$H NMR ($CDCl_3$): δ7.37–7.33 (m, 5H), 5.10 (s, 2H), 4.24–4.03 (m, 6H), 3.97–3.90 (m, 4H), 2.70–2.67 (m, AA'X, 2H), 2.32–2.25 (m, 1H), 1.27 (t, 4H, J 7 Hz), 1.04 (d, 3H, J 7 Hz), 0.69 (d, 3H, J 7 Hz). $^{13}$C NMR ($CDCl_3$) δ164.11, 161.35, 136.31, 128.46, 128.42, 128.05, 127.53, 126.89, 80.41, 66.85, 65.25, 60.85, 60.69, 60.65, 54.43, 31.66, 25.32, 19.054, 16.53, 14.29, 14.21.

d) Ethyl (S)-2-Amino-6-(benzyloxycarbonylamino)-2-hexynoate

To a solution of 1-benzyloxycarbonylamino-4-[(2R,5S)-3,6-diethoxy-2,5-dihydro-2-isopropyl-5-pyrazinyl]but-2-yne (4 g, 9.67 mmol) in dioxane (38 ml) 1M HCl (38.7 ml, 38.7 mmol) was added. This mixture was stirred at ambient temperature overnight. Most of the dioxane was removed at reduced pressure and the aqueous residue diluted with water to 100 ml. This mixture was extracted with ether (100 ml). Then the pH of the solution was adjusted to 9 by addition of concentrated $NH_3$ whereupon a white oil formed. This mixture was extracted with $CHCl_3$ (3×50 ml), the combined $CHCl_3$— layer dried ($MgSO_4$), filtered and concentrated. The residue was subjected to Kugelrohr distillation to remove the ethyl valinate at 50° C. (0.1 torr). The remaining material was pure product.

Yield: 2.57 g (8.44 mmol, 87.3%).

$^1$H NMR ($CDCl_3$): δ7.34 (s, 5H), 5.11 (s, 2H), 4.18 (q, 2H, J 7 Hz), 3.96 (m, 2H), 3.57 (t, 1H, J 6 Hz), 2.60 (AA'X, 2H), 1.27 (t, 3H, J 7 Hz). $^{13}$C NMR ($CDCl_3$): δ173.73, 160.35, 136.24, 128.44, 128.10, 128.05, 79.02, 78.66, 66.93, 61.19, 53.22, 31.15, 25.10, 14.15.

e) (S)-6-(Benzyloxycarbonylamino)-2-9-fluorenylmethyloxycarbonylamino)-4-hexynoic acid To a solution of ethyl (S)-2-amino-6-(benzyloxycarbonylamino)-4-hexynoate HCl (520 mg, 1.71 mmol) in dioxane (5 ml) 1M $NaHCO_3$ (2.05 ml, 2.05 mmol) and water (3 ml). After 5 hours FmocCl (530 mg, 2.05 mmol) in dioxane (5 ml) was added. Almost immediately a precipitate formed. This mixture was acidified by addition of 1M HCl and extracted with $CHCl_3$ (3×30 ml). The organic layer was concentrated and purified by flash chromatography (silica gel; hexane:ethyl acetate:acetic acid 10:10:1).

Yield: 720 mg (1.44 mmol, 84.5%).

$^1$H NMR (300 MHz, DMSO-$d_6$): δ7.87, (d, 2H, J 7.5 Hz), 7.71 (d, 2H, J 7.5 Hz), 7.42–7.28 (m, 9H), 5.00 (s, 2H), 4.30–4.20 (m, 3H), 4.10 (m, 1H), 3.77 (m, 2H), 2.58 (m, 2H). $^{13}$C NMR (300 MHz, DMSO-$d_6$): δ172.41, 156.28, 144.20, 141.10, 137.35, 128.73, 128.21, 128.03, 127.48, 125.68, 120.49, 100.09, 79.37, 79.03, 66.21, 65.93, 53.49, 47.04, 30.63, 21.78.

EXAMPLE 6

(S)-2-Amino-3-(2-furyl) propionic acid a) (2R,5S)-2.5-Dihydro-3,6dimethoxy-2-isopropyl-5-furfurylpyrazine A 1.55M solution of butyllithium (6.45 ml, 10 mmol) in hexane was added by syringe to a stirred solution of (2R)-2,5-dihydro-3,6-dimethoxy-2-isopropylpyrazine (1.84 g, 10 mmol) in THF (50 ml) at −78° C. and the solution stirred for 1 hour at −78° C. A solution of 2-chloromethylfuran (1.3 g, 11 mmol) in THF (10 ml) was added gradually and the stirring continued overnight. The solvent was removed under reduced pressure, the residue dissolved in ethyl acetate (50 ml) and extracted with phosphate buffer (pH 7). The water phase was extracted twice with ethyl acetate (2×20 ml ). The organic layer was dried ($MgSO_4$), solvent evaporated under reduced pressure and the residue purified by flash chromatography (diethyl ether/hexane 15/1, silica gel).

Yield: 2.0 g (76%), colourless viscous liquid.

$^1$H NMR ($CDCl_3$): δ0.65 (d, 3H, J 6.7 Hz), 1.00 (d, 3H, J 6.7 Hz), 2.20 (m, 1H), 3.11 (d, 2H, J 5 Hz), 3.62 (t, 1H, J 3.5 Hz), 3.65 (d, 3H, J 0.9 Hz), 3.70 (d, 3H, J 0.9 Hz), 4.26 (dd, 1H, J 5, J 8.5 Hz), 5.96 (d, 1H, J 3.1 Hz), 6.23 (dd, 1H, J 1.8, J 3.1 Hz), 7.26 (dd, 1H, J 1.0, J 0.8 Hz). $^{13}$C NMR ($CDCl_3$): δ16.54, 19.07, 31.43, 33.03, 52.33, 52.41, 54.95, 60.48, 107.10, 110.24, 141.28, 152.27, 162.53, 164.10.

b) Methyl (S)-2-amino-3-(2-furyl)propionate

A mixture of (2R, 5S)-2,5-dihydro-3,6-dimethoxy-2-isopropyl-5-furfurylpyrazine (2 g, 7.6 mmol), 1M HCl (7.6 ml, 7.6 mmol) and dioxane (7.6 ml) was stirred at ambient temperature overnight under $N_2$. Dioxane was removed under reduced pressure and the water phase extracted with diethyl ether (20 ml). Aqueous ammonia was added to the water phase until pH 9, extracted with CHCl₃ (3×30 ml), dried (MgSO₄) and the solvent removed under reduced pressure. The valine methyl ester was removed by bulb-to-bulb distillation at 40°–50° C. (0.05 mbar). The undistilled title compound was used without further purification.

Yield: 1.0 g (86%).

$^1$H NMR (CDCl₃): δ1.5 (s, 2H), 2.92 (dd, 1H, J 15, J 7.2 Hz), 3.04 (dd, 1H, J 15, J 5 Hz), 3.68 (d, 3H, J 0.5 Hz), 3.73 (dd, 1H, J 7.2, J 5.1 Hz), 6.06 (dd, 1H, J 0.7, J 3.2 Hz), 6.24 (dd, 1H, J 2.9, J 2 Hz), 7.28 (dd, 1H, J 0.7, J 1.9 Hz). $^{13}$C NMR (CDCl₃): δ33.45, 52.00, 53.67, 107.44, 110.20, 141.83, 151.32, 174.97.

c) (S)-2-(9-Fluorenylmethyloxycarbonylamino)-3-(2-furyl)-propionic acid

Methyl (S)-2-amino-3-(2-furyl)propionate (1 g, 6.5 mmol) was mixed with 2M LiOH (3.27 ml, 6.5 mmol) and dioxane (3.27 ml) at 0° C. and stirred overnight under N₂. The next day a TLC control (CHCl₃/MeOH/NH₃ aq 1/1/0.1) of the reaction mixture showed no ester present. 1M NaHCO₃ (9.75 ml, 9.75 mmol) and 9-fluorenylmethyloxycarbonyl chloride (2.5 g, 9.75 mmol) dissolved in dioxane (10 ml) were added to the above solution and the stirring continued for a further 1 hour. Dioxane was removed under reduced pressure and the aqueous solution acidified with a 10% KHSO₄ solution to pH 2. The solution was extracted with CHCl₃ (3×20 ml), dried (MgSO₄), evaporated and purified by flash chromatography (Hexane/ethyl acetate/acetic acid 10/10/1).

Yield: 1.3 g (53%), white crystals.

$^1$H NMR (CDCl₃): δ2.95 (dd, 1H, J 9.9, J 15.2 Hz), 3.08 (dd, 1H, J 4.4, J 15.2 Hz), 3.6 (br.s, 1H), 4.16–4.26 (m, 4H), 6.12 (d, 1H, J 2.9 Hz), 6.33 (t, 1H, J 2.3 Hz), 7.29 (t, 2H, J 7.32 Hz), 7.39 (t, 2H, J 7.48 Hz), 7.49 (br.s, 1H), 7.64 (dd, 2H, J 7.17, J 2.14 Hz), 7.85 (d, 2H, J 7.48 Hz). $^{13}$C NMR (CDCl₃): δ29.8, 46.98, 66.04, 107.45, 110.85, 120.48, 125.57, 125.63, 127.50, 128.07, 141.06, 142.21, 144.09, 151.84, 156.26, 160.35.

EXAMPLE 7

(S)-2-Amino-3-(3,5-dimethyl-4-isoxazolyl)propionic acid a) (2R,5S)-2,5-Dihydro-3,6-dimethoxy-2-isopropyl-5-(3,5-dimethyl-4-isoxazolylmethyl)pyrazine A 1.55M solution of butyllithium (10 ml, 15.5 mmol) in hexane was added by syringe to a stirred solution of (2R)-2,5-dihydro-3,6-dimethoxy-2-isopropylpyrazine (2.85 g, 15.5 mmol) in THF (50 ml) at −78° C. and the solution stirred for 1 hour at −78° C. A solution of 4- chloromethyl-3,5-dimethylisoxazole (2.34 g, 16 mmol) in THF (10 ml) was added gradually and the stirring continued overnight. The solvent was removed under reduced pressure, the residue dissolved in ethyl acetate (50 ml) and extracted with phosphate buffer (pH 7). The water phase was extracted twice with ethyl acetate (2×20 ml). The organic layer was dried (MgSO₄), solvent evaporated under reduced pressure and the residue purified by flash chromatography (diethyl ether/hexane 4/1, silica gel).

Yield: 3 g (64%), colourless viscous liquid.

$^1$H NMR (CDCl₃): δ0.60 (d, 3H, J 6.7 Hz), 0.97 (d, 3H, J 6.7 Hz), 2.17 (s, 3H), 2.26 (s, 3H), 2.73 (dd, 1H, J 5.9, J 14.6 Hz), 2.86 (dd, 1H, J 4.4, J 14.7 Hz), 3.59 (t, 1H, J 3.4 Hz), 3.63 (d, 3H, J 0.3 Hz), 3.68 (d, 3H, J 0.3 Hz), 4.11 (m, 1H). $^{13}$C NMR (CDCl₃): δ10.21, 11.16, 16.41, 18.99, 26.99, 31.29, 52.26, 52.33, 55.93, 60.46, 109.82, 160.18, 162.33, 164.24, 166.34.

b) Methyl (S)-2-amino-3-(3,5-dimethyl-4-isoxazolyl)propionate

A mixture of (2R,5S)-2,5-dihydro-3,6-dimethoxy-2-isopropyl-5-(3,5-dimethyl-4-isoxazolylmethyl)pyrazine (2 g, 6.8 mmol), 1.0M HCl (13.6 ml, 13.6 mmol) and dioxane (13.6 ml) was stirred at ambient temperature overnight under N₂. Dioxane was removed under reduced pressure and the water phase extracted with diethyl ether (20 ml). Aqueous ammonia was added to the water phase until pH 9, extracted with CHCl₃ (3×30 ml), dried (MgSO₄) and the solvent removed under reduced pressure. The valine methyl ester was removed by bulb-to-bulb distillation at 40°–50° C. (0.05 mbar). The undistilled title compound was used without further purification.

Yield: 1.3 g.

$^1$H NMR (CDCl₃): δ1.52 (br.s, 2H), 2.21 (s, 3H), 2.31 (s, 3H), 2.56 (dd, 1H, J 7.5, J 14.6 Hz), 2.74 (dd, 1H, J 6.2, J 14.6 Hz), 3.55 (t, 1H, J 6.7 Hz), 3.69 (s, 3H). $^{13}$C NMR (CDCl₃): δ0.18, 11.06, 27.94, 52.06, 54.45, 109.45, 159.63, 166.31, 175.18.

c) (S)-2- (9-Fluorenylmethyloxycarbonylamino)-3-(3,5-dimethyl-4-isoxazolyl)propionic acid Methyl (S)-2-amino-3-(3,5-dimethyl-4-isoxazolyl) propionate (1.3 g, 6.6 mmol) was mixed with 2M LiOH (3.3 ml, 6.6 mmol) and dioxane (3.3 ml) at 0° C. and stirred overnight under N₂. The next day a TLC control (CHCl₃/MeOH/NH₃ aq 1/1/0.1) of the reaction mixture showed no ester present. 1M NaHCO₃ (10 ml, 10 mmol) and 9-fluorenylmethyloxycarbonyl chloride (2.6 g, 10 mmol) dissolved in dioxane (10 ml) were added to the above solution and the stirring continued for a further hour. Dioxane was removed under reduced pressure and the aqueous solution acidified with a 10% KHSO₄ solution to pH 2. The solution was extracted with CHCl₃ (3×20 ml), dried (MgSO₄) evaporated and purified by flash chromatography (Hexane/ethyl acetate/acetic acid 10/10/1).

Yield: 1.6 g (59%), white crystals.

$^1$H NMR (CDCl₃): δ2.10 (s, 3H), 2.19 (s, 3H), 2.65 (dd, 1H, J 9.46, J 14.65 Hz), 2.76 (dd, 1H, J 5.4, J 14.65 Hz), 3.5–4.2 (m, 4H), 7.24–7.40 (m, 4H), 7.63 (d, 2H, J 7.32 Hz), 7.82 (t, 2H, J 7.63 Hz). $^{13}$C NMR (CDCl₃): δ10.02, 10.90, 24.27, 46.94, 53.81, 66.73, 110.16, 120.44, 125.51, 127.46, 128.06, 141.06, 144.12, 156.27, 159.83, 166.51, 173.02.

Solid-phase synthesis of peptides

Solid-phase peptide synthesis was carried out essentially according to the principles of the fluorenylmethoxycarbonyl (Fmoc)-polyamide strategy (Atherton & Sheppard, *Solid phase peptide synthesis: a practical approach*. Oxford: IRL Press at Oxford University Press, 1989). Commercially available synthesis resins were used; for batch synthesis either manually or using a semi-automatic instrument (Labortec Peptide Synthesizer 5P 650) these were of polystyrene with acid-labile (Wang, *J. Am, Chem. Soc.*, 95, 1328–1333, 1973) or acid hyperlabile linkage agents (Merger et al., *Tetrahedron Letters* 29, 4005–4008, 1988). Alternatively, peptides were assembled in fully automatic mode on flow resins (Atherton et al., *J. Chem. Soc., Chem. Commun.*, 1151–2, 1981) using an LKB Biolynx 4170 Automated Peptide Synthesizer. Synthesis resins were purchased which already contained the protected desired C-terminal Fmoc-amino acid residue. Chain elongation was achieved variously with side-chain protected Fmoc-amino acid pentafluorophenyl esters (Kisfaludy & Schoen, *Synthesis*, 325–327, 1983), using activation with dicyclohexylcarbodiimide (DCC)/1-hydroxybenzotriazole (HOBt) (Koenig & Geiger, *Chem. Ber.* 103, 2034–2040, 1970) or using the coupling reagent PyBOP (Coste et al., *Tetrahedron*

Lett., 31, 205–208, 1990). The lysine side-chain amino group was protected with the t-butyloxycarbonyl function, the side-chain carboxy groups of glutamic and aspartic acid were protected as the t-butyl esters.

After complete solid-phase assembly of the desired sequences, the peptides were cleaved from the synthesis resins with concomitant side-chain deprotection using trifluoroacetic acid to which suitable scavenger chemicals (King et al., *Int. J. Peptide Protein RES.*, 36 255–268, 1990) had been added. After evaporation, the peptides were isolated by precipitation with diethyl ether and drying. Purification was by preparative reversed phase high performance liquid chromatography.

TABLE 1

Analytical data for monomeric peptides with the general structure
Pyr—Glu—Asp—Xaa—Lys—OH SEQ ID NO 3

| Xaa[a] | HPLC Method[b] (Retention time, min) | Purity[c] (%) | FAB-MS [M + H]$^+$ |
|---|---|---|---|
| Valine | 0-30-20 (17) | 100 | 601.4 |
| Norleucine | 0-30-20 (23) | 99 | 615.4 |
| Leucine | 0-30-20 (22) | 98 | 615.4 |
| Tryptophan | 20-50-20 (14) | 96 | 688.3 |
| Tyrosine | 0-30-20 (13) | 98 | |
| Lysine | 0-30-20 (10) | 100 | 630.4 |
| Glutamic acid | 0-30-20 (12) | 99 | 631.6 |
| Glutamine | 0-30-20 (12) | 100 | 630.3 |
| Histidine | 0-30-20 (13) | 99 | 639.4 |
| Proline | 0-30-20 (15) | 99 | 599.3 |
| 1-Naphthylalanine | 30-90-20 (15) | 99 | 699 |
| Thien-2-ylalanine | 0-30-20 (20) | 100 | 655.3 |
| Pyridin-2-ylalanine | 0-30-20 (12) | 95 | |
| Furan-2-ylalanine | | | |
| 3,5-Dimethylisoxazol-4-ylalanine | | | |
| Cyclohexylalanine | 10-40-20 (23) | 98 | 655.4 |
| Allylglycine | | | |
| O-Methylserine | | | |
| 2-Amino-6-azidohexanoic acid | | | |
| 2-Amino-4,5-dihydroxy-6-benzyloxycarbonylaminohexanoic acid | | | |

[a]All amino acids have the L configuration, i.e., that found in natural amino acids
[b]The methods are expressed as gradients of mobile phase B in A over time, thus e.g. 10-40-20 refers to a gradient starting at 10 and finishing at 40% B over 20 min. Mobile phases: A) 0.1% TFA B) 0.1% TFA in 40% MeCN. Column: Vydac TP54,C18,0.46 × 25 cm, 5 µm particles, 100 Å pore; flow 1 mL/min
[c]Refers to integration of HPLC chromatogram peaks ($\lambda$ = 215 nm)

HOBt=Hydroxybenzotriazole
Pfp=Pentafluorophenyl
Fmoc=9-Fluorenylmethoxycarbonyl
Boc=t-Butoxycarbonyl
DCC=Dicyclohexylcarbodiimide
Cin=(S)-2-Amino-5-phenyl-4-(E)-penten-1-oic acid.
BuLi=n-butyllithium
THF=tetrahydrofuran
DMF=dimethylformamide pGlu-Glu-Asp-[Cin]-Lys SEQ ID NO 4

The peptide is synthesized using a Labortec Peptide Synthesizer. Fmoc-Lys(Boc)-Sasrin polymer (1.0 g, 0.6 mmol; Bachem A. G.; substitution 0.6 mmol/g) is charged into a 100 ml reaction flask. (S)-2-(9-Fluorenylmethoxycarbonylamino)-5-phenyl-4-(E)-penten-1-oic acid (578 mg, 1.4 mmol), DCC (290 mg, 1.4 mmol) and HOBt (211 mg, 1.4 mmol) in DMF (20 ml) are added to the polymer and the reaction allowed to proceed for 9 hours. The polymer is then washed with $CH_2Cl_2$, with 30% MeOH in $CH_2Cl_2$ and with DMF (negative Kaiser test).

The remaining part of the synthesis is carried out by standard protocol using Fmoc-Asp(OtBu)-Opfp (0.89 g, 1.5 mmol), Fmoc-Glu(OtBu)-Opfp (0.90 g, 1.5 mmol) and pGlu-pentachlorophenyl ester (0.57 g, 1.5 mmol). HOBt (0.23 mg, 1.5 mmol) is added in each coupling step which is allowed to proceed for 1 hour. Completion of the coupling is ascertained by negative Kaiser test. After the coupling with the Fmoc-amino acid the polymer is washed with DMF, the protecting group cleaved off by 20% piperidine in DMF, and the polymer again washed with DMF. After the final coupling the polymer is washed with MeOH/$CH_2Cl_2$ and $CH_2Cl_2$ and dried. The peptide is cleaved from the polymer by TFA:$CH_2Cl_2$ 1:1, the solution freeze-dried, the residue dissolved in water, filtered (0.45 µ) and the filtrate freeze-dried. For further purification the crude peptide is dissolved in water and subjected to preparative HPLC on Beckman Ultrasphere ODS and solutions A 0.1% TFA in $H_2O$, B 0.1% TFA in MeCN:$H_2O$ 40:60. The pure peptide (>95%) is obtained after freeze-drying of the fractions collected which contain the homogenous peptide.

TABLE 2

Amino acid analysis data for peptides
Peptide with Xaa in Pyr—Glu—Asp—Xaa—Lys—OH SEQ ID NO 4

| | Xaa=Val | Xaa=Leu | Xaa=Nle | Xaa=Ser | Xaa=Trp |
|---|---|---|---|---|---|
| | | | Number of residues found (theory) | | |
| Val | 0.81(1) | | | | |
| Nle | | | 0.94(1) | | |
| Leu | | 0.97(1) | | | |
| Trp | | | | | 0.51[a](1) |
| Lys | 0.77(1) | 0.68(1) | 0.89(1) | 0.90(1) | 1.00(1) |
| Glu | 2.09(2) | 2.01(2) | 2.11(2) | 2.11(2) | 2.33(2) |
| Asp | 1.00(1) | 1.00(1) | 1.00(1) | 1.00(1) | 0.68(1) |

[a]Tryptophan is partly destroyed during acid hydrolysis.

We claim:

1. A peptide compound derivative comprising a single chain hemoregulatory peptide of formula:

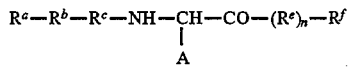

wherein $R^a$ represents

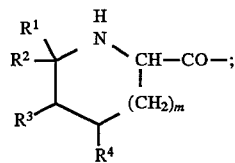

$R^b$ represents 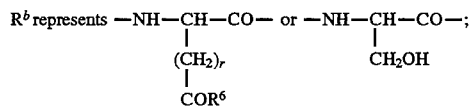

$R^c$ represents 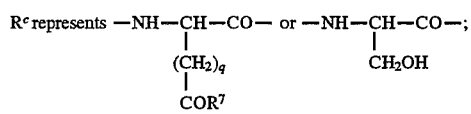

$R^e$ represents 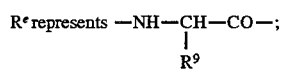

$R^f$ represents 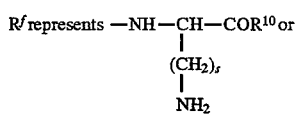

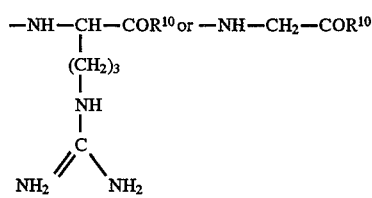

and A is a group —$CR^4R^{A'}$—Z, wherein n and m independently represent 0 or 1;

q and r independently represent 1 or 2;

s represents 3 or 4;

$R^1$ and $R^2$ are both hydrogen atoms or, when m=0, $R^1$ and $R^2$ together represent an oxo group;

$R^3$ and $R^4$ are both hydrogen atoms or together represent a carbon-carbon bond;

each $R^6$ and $R^7$ independently represents a hydroxy group or an amino group;

$R^9$ represents hydrogen or a methyl group; and $R^{10}$ represents a hydroxy or amino group, the residue of the amino acid glutamine or a peptide having an N-terminal glutamine unit, each $R^A$ is independently a hydrogen atom or a group —$R^{A''}$, —$OR^{A''}$, —$SR^{A''}$, —$NR^{A''}R^{A''}$, $CONR^{A''}R^{A''}$ or —$COOR^{A''}$;

$R^{A'}$ is a hydrogen atom or a group $R^{A''}$;

$R^{A''}$ is an alkyl, cycloalkyl, alkanoyl, hydroxyalkyl, amidine group or a carbocyclic or heterocyclic group;

Z is a group —$OR^B$, —$NR^CR^C$, —$CR^DR^ER^F$ or a substituted or unsubstituted, aromatic or non-aromatic, carbocyclic or heterocyclic ring other than unsubstituted phenyl;

each $R^B$ is a straight chained or branched, saturated or unsaturated hydrocarbon group optionally substituted by hydroxyl, amino or azide groups or by one or more $R^A$ groups, where $R^A$ is as defined above, and optionally interrupted by one or more —N—, —O— or —S— heteroatoms;

$R^C$ is a hydrogen atom or a group $R^B$;

$R^D$ is a hydrogen atom or a group $R^F$;

$R^E$ is a hydrogen atom or a group $R^F$, or together with the carbon atom of the $CR^DR^ER^F$ group, $R^E$ and $R^D$ form a C=O group; and $R^F$ is a group —$R^B$, —$OR^B$, —$NR^CR^C$ or —$SR^B$, or a hydroxy, carboxy, aminocarbonyl or alkoxy group, or is a methylene group linked to the nitrogen atom of the —NH—CH (A)—CO—group, or together with $R^D$ forms an alkylidene group, or is a hydrogen atom where one of $R^A$, $R^{A'}$, $R^D$ and $R^E$ is other than hydrogen.

2. A peptide compound derivative as claimed in claim 1 wherein —A is a group

—$CH_2$—Z wherein Z is a group —$OR^B$, where $R^B$ is as defined in claim 1 or —$CHR^DR^F$;

$R^D$ represents a hydrogen atom or a group —$CH_3$;

$R^F$ represents an alkyl group optionally substituted by hydroxyl, amino or azide groups; or $R^D$ and $R^F$ together form an alkylidine group.

3. A peptide compound derivative as claimed in claim 1 wherein in a peptide chain of formula I n represents 0.

4. A peptide compound derivative as claimed in claim 1 wherein in a peptide chain of formula I m represents 0.

5. A pharmaceutical composition comprising a peptide compound derivative as claimed in claim 1 together with a pharmaceutical carrier or excipient.

6. A method of inhibiting cell division in a patient, said method comprising administering to said patient an effective amount of a peptide compound derivative as claimed in claim 1.

7. A method as claimed in claim 6 wherein division of myelopoietic or bone marrow cells is inhibited.

8. A process for producing a peptide compound derivative as claimed in claim 1 comprising deprotecting a partially or fully protected derivative thereof.

9. Lactim dipeptide ethers of formula $$\text{CH}_3\text{O}-\overset{\text{A}}{\underset{}{\text{C}}}\cdots\text{N}=\overset{\text{CH}_3}{\underset{\text{OCH}_3}{\text{C}-\text{CH}_3}}$$

wherein —A is as defined in claim 1 and when $R^A$ and $R^{A'}$ each represent hydrogen then Z is other than a substituted aromatic carbocyclic or heterocyclic ring.

10. Amino protected, hydroxyl protected, thiol protected and/or carboxyl protected derivatives of a peptide compound derivative comprising a single-chain hemoregulatory peptide of formula:

$$R^a—R^b—R^c—NH—\underset{A}{\text{CH}}—CO—(R^e)_n—R^f$$

wherein $R^a$ represents
$$R^2-\underset{R^3}{\overset{R^1}{\text{—}}}\overset{H}{\underset{R^4}{\text{N}}}\diagdown\text{CH—CO—}\atop(\text{CH}_2)_m$$

$R^b$ represents —NH—CH—CO— or —NH—CH—CO—;
  |                                    |
  (CH$_2$)$_r$                         CH$_2$OH
  |
  COR$^6$ $R^c$ represents —NH—CH—CO— or —NH—CH—CO—;
  |                                    |
  (CH$_2$)$_q$                         CH$_2$OH
  |
  COR$^7$ $R^e$ represents —NH—CH—CO—;
  |
  R$^9$ $R^f$ represents —NH—CH—COR$^{10}$ or
  |
  (CH$_2$)$_s$
  |
  NH$_2$ —NH—CH—COR$^{10}$ or —NH—CH$_2$—COR$^{10}$
  |
  (CH$_2$)$_3$
  |
  NH
  |
  C
  ⫽ \
  NH$_2$  NH$_2$ and A is a group —CR$^4$R$^{A'}$—Z,
wherein n and m independently represent 0 or 1;
q or r independently represent 1 or 2;
s represents 3 or 4;
$R^1$ and $R^2$ are both hydrogen atoms or, when m=0, $R^1$ and $R^2$ together represent an oxo group;
$R^3$ and $R^4$ are both hydrogen atoms or together represent a carbon-carbon bond;
each $R^6$ and $R^7$ independently represents a hydroxy group or an amino group;
$R^9$ represents hydrogen or a methyl group; and
$R^{10}$ represents a hydroxy or amino group, the residue of the amino acid glutamine or a peptide having an N-terminal glutamine unit, each $R^A$ is independently a hydrogen atom or a group —$R^{A''}$, —$OR^{A''}$, —$SR^{A''}$, —$NR^{A''}R^{A''}$, $CONR^{A''}R^{A''}$ or —$COOR^{A''}$;

$R^{A'}$ is a hydrogen atom or a group $R^{A''}$;

$R^{A''}$ is an alkyl, cycloalkyl, alkanoyl, hydroxyalkyl, amidine group or a carbocyclic or heterocyclic group;

Z is a group —$OR^B$, —$NR^CR^C$, —$CR^DR^ER^F$ or a substituted or unsubstituted, aromatic or non-aromatic, carbocyclic or heterocyclic ring other than unsubstituted phenyl;

each $R^B$ is a straight chained or branched, saturated or unsaturated hydrocarbon group optionally substituted by hydroxyl, amino or azide groups or by one or more $R^A$ groups, where $R^A$ is as defined above, and optionally interrupted by one or more —N—, —O— or —S— heteroatoms;

$R^C$ is a hydrogen atom or a group $R^B$;

$R^D$ is a hydrogen atom or a group $R^F$;

$R^E$ is a hydrogen atom or a group $R^F$, or together with the carbon atom of the $CR^DR^ER^F$ group, $R^E$ and $R^D$ form a >C=O group; and $R^F$ is a group —$R^B$, —$OR^B$, —$NR^CR^C$ or —$SR^B$, or a hydroxy, carboxy, aminocarbonyl or alkoxy group, or is a methylene group linked to the nitrogen atom of the —NH—CH(A)—CO— group, or together or with $R^D$ forms an alkylidene group, or is a hydrogen atom where one of $R^A$, $R^{A'}$, $R^D$ and $R^E$ is other than hydrogen.

11. A peptide compound derivative comprising a single chain hemoregulatory peptide of formula:

$$R^a—R^b—R^c—NH—\underset{A}{\text{CH}}—CO—(R^e)_n—R^f$$

wherein $R^a$ represents
$$R^2-\underset{R^3}{\overset{R^1}{\text{—}}}\overset{H}{\underset{R^4}{\text{N}}}\diagdown\text{CH—CO—}\atop(\text{CH}_2)_m$$

$R^b$ represents —NH—CH—CO— or —NH—CH—CO—;
  |                                    |
  (CH$_2$)$_r$                         CH$_2$OH
  |
  COR$^6$ $R^c$ represents —NH—CH—CO— or —NH—CH—CO—;
  |                                    |
  (CH$_2$)$_q$                         CH$_2$OH
  |
  COR$^7$ $R^e$ represents —NH—CH—CO—;
  |
  R$^9$ $R^f$ represents —NH—CH—COR$^{10}$ or
  |
  (CH$_2$)$_s$
  |
  NH$_2$ -continued —NH—CH—COR¹⁰ or —NH—CH₂—COR¹⁰

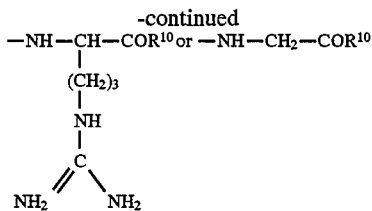

and A is a group —CR^A R^A'—Z,
wherein n and m independently represent 0 or 1;
q and r independently represent 1 or 2;
s represents 3 or 4;
R¹ and R² are both hydrogen atoms or, when m=0, R¹ and R² together represent an oxo group;
R³ and R⁴ are both hydrogen atoms or together represent a carbon-carbon bond;
each R⁶ and R⁷ independently represents a hydroxy group or an amino group;
R⁹ represents hydrogen or a methyl group; and
R¹⁰ represents a hydroxy or amino group, the residue of the amino acid glutamine or a peptide having an N-terminal glutamine unit,
each $R^A$ is independently a hydrogen atom or a group —$R^{A"}$, —$OR^{A"}$, —$SR^{A"}$, —$NR^{A"}R^{A"}$, $CONR^{A"}R^{A"}$ or —$COOR^{A"}$;
$R^{A'}$ is a hydrogen atom or a group $R^{A"}$;
$R^{A"}$ is an alkyl, cycloalkyl, alkanoyl, hydroxyalkyl, amidine group or a carbocyclic or heterocyclic group;
Z is a substituted or unsubstituted, aromatic or non-aromatic, carbocyclic or heterocyclic ring other than unsubstituted phenyl.

12. A peptide compound derivative as claimed in claim 11 wherein —A is

—CH₂—Z wherein Z represents a substituted or unsubstituted, aromatic or non-aromatic, carbocyclic or heterocyclic ring other than unsubstituted phenyl.

13. A peptide compound derivative as claimed in claim 12 wherein Z represents a benzyl, indolyl, hydroxyphenyl, imidazolyl, naphthyl, thienyl, pyridinyl, furanyl, isoxazolyl, 3,5-dimethylisoxazolyl or cyclohexyl group.

14. A peptide compound of formula

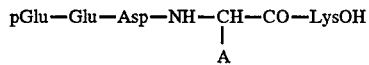

wherein

A is a group —$CR^A R^{A'}$—Z;

in which $R^A$ is a hydrogen atom or a group —$R^{A"}$, —$OR^{A"}$, —$SR^{A"}$, —$NR^{A"}R^{A"}$, $CONR^{A"}R^{A"}$ or —$COOR^{A"}$;

$R^{A'}$ is a hydrogen atom or a group $R^{A"}$;

$R^{A"}$ is an alkyl, cycloalkyl, alkanoyl, hydroxyalkyl, amidine group or a carbocyclic or heterocyclic group;

Z is a group —$OR^B$, —$NR^C R^C$, —$CR^D R^E R^F$ or a substituted or unsubstituted, aromatic or non-aromatic, carbocyclic or heterocyclic ring other than unsubstituted phenyl;

wherein each $R^B$ is a straight chained or branched, saturated or unsaturated hydrocarbon group optionally substituted by hydroxyl, amino or azide groups or by one or more $R^A$ groups, where $R^A$ is as defined above, and optionally interrupted by one or more —N—, —O— or —S— heteroatoms;

$R^C$ is a hydrogen atom or a group $R^B$;

$R^D$ is a hydrogen atom or a group $R^F$;

$R^E$ is a hydrogen atom or a group $R^F$, or together with the carbon atom of the $CR^D R^E R^F$ group, $R^E$ and $R^D$ form a >C=O group; and $R^F$ is a group —$R^B$, —$OR^B$, —$NR^C R^C$ or —$SR^B$, or a hydroxy, carboxy, aminocarbonyl or alkoxy group, or is a methylene group linked to the nitrogen atom of the —NH—CH(A)—CO— group, or together with $R^D$ forms an alkylidene group, or is a hydrogen atom where one of $R^A$, $R^{A'}$, $R^D$ and $R^E$ is other than hydrogen.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /label=pE
            / note="pE=pyroglutamic acid"

( x i ) SEQUENCE DESCRIPTION: SEQ ID NO: 1:

Xaa   Glu   Asp   Cys   Lys
      1                       5

( 2 ) INFORMATION FOR SEQ ID NO: 2:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 2:

Lys   Ile   Ile   His   Glu   Asp   Gly   Tyr   Ser
      1                       5

( 2 ) INFORMATION FOR SEQ ID NO: 3:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /label=pE
            / note="pE=pyroglutamic acid"

( x i ) SEQUENCE DESCRIPTION: SEQ ID NO: 3:

Xaa   Glu   Asp   Xaa   Lys
      1                       5

( 2 ) INFORMATION FOR SEQ ID NO: 4:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 4
      ( D ) OTHER INFORMATION: /label=Cin /note="Cin=(S)-2-amino-5
            - phenyl-4-(E)-penten-1-oic acid"

(xi) SEQUENCE DESCRIPTION: SEQ ID NO: 4:

```
Glu  Glu  Asp  Xaa  Lys
 1                  5
```